United States Patent [19]
Shechter et al.

[11] Patent Number: 5,776,970
[45] Date of Patent: Jul. 7, 1998

[54] TRYPTOPHAN DERIVATIVES AS PROTEIN TYROSINE KINASE BLOCKERS AND THEIR USE IN THE TREATMENT OF NEOPLASTIC DISEASES

[75] Inventors: Yoram Shechter, Rehovot; David Naor, Jerusalem, both of Israel

[73] Assignees: Yeda Research and Development Co. Ltd., Rehovot; Yissum Research Development Co., Jerusalem, both of Israel

[21] Appl. No.: 234,159

[22] Filed: Apr. 28, 1994

[51] Int. Cl.[6] .................. C07D 401/02; C07D 209/10; A61K 31/47; A61K 31/405
[52] U.S. Cl. ................. 514/419; 548/496; 514/339; 514/421; 546/277.4
[58] Field of Search ............. 548/496; 546/277.4; 514/339, 419, 421

[56] References Cited

PUBLICATIONS

Levitski, Alexander. "Tyrphostins: tyrosine kinase blockers as novel antiproliferative agents and dissectors of signal transduction." FASEB J. 6, 3275–3282. (1992).

Rodbell, Martin. "Metabolism of Isolated Fat Cells." J. Biol. Chem. 239, 375–380. (1963).

Shisheva, Assia et al. "A novel approach for evaluating tyrosine kinase activity based on the radioimmunological determination of phosphotyrosine." J. Biol. Chem. Methods 23, 307–314. (1991).

Bishop, J. M. (1987) "The Molecular Genetics of Cancer." Science. 335, 305–311.

Elder, James T. et al. (1989) "Overexpression of Transforming Growth Factor α in Psoriatic Epidermis." Science. 243, 811–814.

Graziani, Y. et al. (1981) "Regulation of Protein Kinases Activity by Quercetin inEhrlich Ascites Tumor Cells." Biochim. Biophys. Acta 714, 415–421.

Graziani, Y. et al. (1983) "The effect of quercetin on the phosphorylation activity of the Rous sarcoma virus transforming gene product in vitro and in vivo." Eur.J. Biochem. 135, 583–589.

Ross, R. (1989) "Platelet–Derived Growth Factor." Lancet 1, 1179–1182.

Shechter, Y. (1982) "Evaluation of Adenosine of Related Nucleosides as Physiological Regulators of Lipolysis in Adipose Tissue." Endocrinology. 110, 1579–1583.

Shisheva, A. et al. (1993) "Role of Cytosolic Tyrosine Kinase in Mediating Insulin–like Actions of Vanadate in Rat Adipocytes." J. Biol. Chem. 268, 6463–6469.

Primary Examiner—David B. Springer
Attorney, Agent, or Firm—Browdy and Neimark

[57] ABSTRACT

Tryptophan derivatives substituted by a hydrophobic group, e.g. carbobenzoxy, at the N-terminus, and a hydrophilic group, e.g. —COOH, —$SO_3H$ or —$PO_3H$, at the C-terminus, were found to be cell-permeable blockers of protein tyrosine kinases (PTKs). These PTK blockers are useful in basic research and in the treatment of neoplastic diseases.

8 Claims, 4 Drawing Sheets

TRYPTOPHAN DERIVATIVES AS PROTEIN TYROSINE KINASE BLOCKERS AND THEIR USE IN THE TREATMENT OF NEOPLASTIC DISEASES

FIELD AND BACKGROUND OF THE INVENTION

The present invention relates to new tryptophan derivatives and to pharmaceutical compositions comprising them, particularly for the treatment of neoplastic diseases.

Protein tyrosine kinases (PTKS) are members of a growing family of protooncoproteins and oncoproteins that play a pivotal role in normal and abnormal proliferative processes. Enhanced PTK activity has been associated with proliferative diseases such as cancer (Bishop, 1987), atherosclerosis (Ross, 1989) and probably psoriasis (Elder et al., 1989). Correlation between increased PTK activity and a particular pathological condition was demonstrated in mammary and ovarian carcinoma (reviewed in Levitzki, 1992).

One of the ideas to control growth and proliferation of malignant cells in vitro and in vivo is the utilization of cell-permeable blockers of tyrosine kinases (PTK blockers) (Graziani et al., 1981 and 1983). Ideally, a specific inhibitor for each one of the tyrosine kinase involved is desirable. However, a broader specificity may be preferable as more than one family member of these enzymes may be involved in abnormal proliferative processes (Levitzki, 1992).

Conceptually, even in cases in which an enzyme, its substrate and the catalytic mechanism have been well characterized, there is no certain rational approach for designing an enzyme blocker. In spite of the need for PTK-blockers—for basic research and therapeutical purposes, this field has progressed slowly, mainly due to the lack of rational-designing techniques to produce PTK blockers.

Since PTKs are involved in many vital processes, it would be highly desirable to select PTK-blockers arresting neoplastic proliferation but which are less effective in inhibiting normal metabolic signals which are also dependent on endogenous tyrosine kinase activity.

SUMMARY OF THE INVENTION

It has now been found in accordance with the present invention that certain tryptophan derivatives of hydrophobic nature can permeate into cell interiors and inhibit the insulin receptor tyrosine kinase (InsRTK) as well as several related PTKs.

The PTK-blockers of the invention were developed by an approach termed "induced-fit reverse chemical modification" which enables to design a PTK-blocker also if the basic physicochemical features of the enzyme are largely obscured. The method is based on chemical modification and inactivation of the enzyme with a substrate-like reagent followed by modification of the reagent (rather than the enzyme itself) and finally converting it to non-covalent blocker.

Thus, to design and synthesize a low molecular weight blocker of InsRTK able to permeate into cell interiors, we first searched for an affinity reagent that would covalently bind and inactivate the InsRTK at low concentrations. Such a reagent was found to be benzyloxycarbonylphenyl-N-hydroxysuccinimide ester (CBZ-Phe-OSU) that inactivated InsRTK with an $IC_{50}$ value=50 µM. Examining the inactivation power of CBZ-Phe-OSU and related analogs, revealed that the modifying reagent should possess (from the N-terminus to the C-terminus side) a small aromatic hydrophobic domain; a big hydrophobic domain and a C-terminus hydrophilic domain. The complementary hydrophilic domain of the InsRTK contains a lysine moiety that reacts covalently with the active ester and is likely to participate in substrate binding or catalysis. Equipped with this information we have synthesized a family of competitive inhibitors.

The present invention thus relates to a compound of formula I:

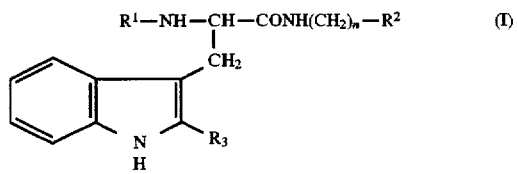

wherein $R^1$ is a hydrophobic group;

$R^2$ is —COOH, —$SO_3H$ or —$PO_3H$;

$R^3$ is H, or phenylthio or pyridythio substituted by one or two $NO_2$ groups;

n is 1 to 3, and pharmaceutically acceptable salts thereof.

In the compound of formula I, $R^1$ is a hydrophobic group enabling permeation of the compound to the cell interior. Examples of suitable hydrophobic groups are $C_5$–$C_{20}$ alkyl or alkenyl, $C_5$–$C_{20}$ carboxylic acyl, $C_3$–$C_8$ alkoxycarbonyl, $C_5$–$C_8$ cycloalkoxycarbonyl, and unsubstituted or substituted benzyloxycarbonyl.

Suitable "$C_5$–$C_{20}$, alkyl" groups according to the invention include, but are not limited, to the following: straight and branched pentyl, hexyl, octyl, dodecyl, etc. The groups "$C_5$–$C_{20}$ alkenyl" include, but are not limited to, straight and branched pentenyl, hexenyl, octenyl, dodecenyl, etc. The radicals "$C_5$–$C_{20}$ carboxylic acyl" herein refers to saturated or unsaturated, straight or branched chain radicals including, but not being limited to, valeryl, caproyl, capryl, lauryl, myristil, palmitoyl, stearoyl, arachidoyl, palmitoleyl, oleyl, etc. "$C_3$–$C_8$ alkoxycarbonyl" herein refers to straight or branched radicals including, but not being limited to, isopropoxycarbonyl, t-butoxycarbonyl (t-Boc), t-amyloxycarbonyl, pentoxycarbonyl, hexoxycarbonyl, etc. "$C_5$–$C_8$ cycloalkoxycarbonyl" radicals include cyclopentoxycarbonyl, cyclohexoxycarbonyl, cycloheptyloxycarbonyl and cyclooctyloxycarbonyl. "Substituted benzyloxycarbonyl" groups include, but are not limited to, o-chlorobenzyloxycarbonyl, p-chlorobenzyloxycarbonyl and 2,4- and 2,6-dichlorobenzyloxycarbonyl.

In preferred embodiments according to the invention, $R^1$ is benzyloxycarbonyl (carbobenzoxy, denoted herein as CBZ) or t-butoxycarbonyl (t-Boc) and $R^2$ is —$SO_3H$. Some of these compounds are shown in Scheme I herein with their chemical formulas and respective designations as used herein in the specification. In a still more preferred embodiment, the invention relates to the compound in which $R^1$ is carbobenzoxy, $R^2$ is $SO_3H$, $R^3$ is 2,4-dinitrophenylthio and n is 2 herein designated as CBZ-DNPS-TRP-TAU.

SCHEME I

| Derivative designation | Structure |
| --- | --- |
| L-tryptophan | NH$_2$CH—COOH, CH$_2$-(indole) |
| AC-TRP-TAU | AC—NH—CH—CONH—(CH$_2$)$_2$SO$_3^-$, CH$_2$-(indole) |
| CBZ-TRP-β-TAU | CBZ—NH—CH—CONH(CH$_2$)$_3$SO$_3^-$, CH$_2$-(indole) |
| CBZ-TRP-TAU | CBZ—NH—CH—CONH(CH$_2$)$_2$—SO$_3^-$, CH$_2$-(indole) |
| CBZ-NPS-TRP-TAU | CBZ—NH—CH—CONH(CH$_2$)$_2$—SO$_3^-$, CH$_2$-(indole-2-S-(o-NO$_2$-C$_6$H$_4$)) |
| CBZ-DNPS-TRP-TAU | CBZ—NH—CH—CONH(CH$_2$)$_2$—SO$_3^-$, CH$_2$-(indole-2-S-(2,4-(NO$_2$)$_2$-C$_6$H$_3$)) |

Any pharmaceutically acceptable salt of the compounds of formula I with organic or inorganic bases may be used according to the invention, such as sodium salts.

The compounds of formula I are prepared by a process comprising reaction of R$^1$-L-tryptophan-N-hydroxysuccinimide with a compound R$^2$—(CH$_2$)$_n$—NH$_2$, thus obtaining a compound of formula I in which R$^3$ is H, which is optionally further reacted with a compound of formula R$^3$—Cl to produce compounds in which R$^3$ is other than hydrogen. Thus, for example, the above compound CBZ-DNPS-TRP-TAU is prepared by first reacting carbobenzoxy-L-tryptophan-N-hydroxy-succinimide ester (CBZ-TRP-OSU) with taurine (TAU), and the resulting CBZ-TRP-TAU compound is reacted with 2,4-dinitrophenylsulfenyl chloride (2,4-DNPS-Cl). By substituting taurine with other suitable amino sulfonic, amino carboxylic or aminophosphonic acids, other derivatives of formula I are obtained.

The compounds of formula I are useful for basic research on protein tyrosine kinases. They may be further used as active ingredients of pharmaceutical compositions for the treatment of cancer, together with pharmaceutically acceptable carriers. Cancers that can be treated with the compounds of the invention are those with high rate of proliferation, e.g., non-Hodgkins lymphomas of B- or T-cell origin and most types of leukemia. In addition, the compounds of formula I may be efficient in blocking fast spreading metastasis of solid tumors, e.g., breast cancer, rectocolon cancer and lung cancer, and in the disseminated phase of malignant melanoma. The compositions will be administered by any suitable way, e.g., by injection, in a dose to be established by the specialists depending on the age of the patient and gravity of the disease. Doses of from 3 mg/kg body weight to 10 mg/kg body weight can be used.

In a further embodiment, the invention relates to a method of treatment of a patient afflicted with a neoplastic disease which comprises administering to said patient an effective amount of a compound of formula I.

DESCRIPTION OF PREFERRED EMBODIMENTS

The invention will now be illustrated by the following non-limiting examples.

EXAMPLE 1

Synthesis of CBZ-DNPS-TRP-TAU

I. Synthesis of CBZ-TRP-TAU 870 mg (2 eq) of CBZ-L-tryptophan-N-hydroxysuccinimide ester (CBZ-TRP-OSU) were dissolved in 20 ml of dimethylsulfoxide (DMSO). Taurine (TAU, 2-aminoethylsulfonic acid (124 mg, 1 eq) and NaHCO$_3$ (168 mg, 2 eq) were dissolved in 20 ml of water. The solutions were then mixed quickly and allowed to react for 7 hours at room temperature. Water (200 ml) was then added and the reaction mixture was lyophilized to dryness.

The residue was dissolved in 140 ml of water. The suspension was brought to pH 3.0 by adding the proper amount of HCl and extracted with ethyl acetate (EtAc). Extraction was repeated 4–7 times, until no absorbance at 280 nm was detected in the EtAc fraction. The aqueous solution was lyophilized; CBZ-TRP-TAU is highly soluble in H$_2$O (up to a concentration of 1.3M). Molar extinction coefficient $\epsilon_{280\ nm}$=5500 at neutral pH value. It contains one to one (molar ratio) of tryptophan to taurine as determined by absorbance at 280 nm and amino acid analysis following acid hydrolysis.

II. CBZ-DNPS-TRP-TAU

CBZ-TRP-TAU (final concentration=5 mM in 200 ml, 98% glacial acetic acid) was allowed to react with 2 equivalents of 2,4-dinitrophenylsulfenyl chloride (2,4 DNPS-Cl) for several hours at room temperature. Excess reagents were then centrifuged down, and acetic acid evaporated. The residue was dissolved in 200 ml of 0.1M NaOH and centrifuged again. The clear solution was extracted with EtAc, several times. Before each extraction the aqueous phase was adjusted to pH 10 and reextracted (This procedure was applied since in preliminary experiments it was found that CBZ-DNPS-TRP-TAU (but not CBZ-TRP-TAU) is extractable to ethyl acetate at alkaline pH values). The EtAc fractions were pooled together, dried by sodium sulphate and evaporated. The residue was suspended in H$_2$O and lyophilized, thus obtaining the title product. CBZ-DNPS-TRP-TAU is soluble in H$_2$O (up to a concentration of 2 mM) and in DMF, or DMSO (at 20 mM concentration). It has molar extinction coefficients (in 20% acetic acid) with maxima at 280 nm ($\epsilon_{280\ nm}$=33,400) and at 360 nm ($\epsilon_{360\ nm}$=16,000). Amino acid analysis (after acid hydrolysis) revealed nearly 1 to 1 molar ratio of taurine to DNPS-TRP. IC$_{50}$ value=0.13 mM.

EXAMPLE 2

Synthesis of CBZ-DNPS-TRP-aminomethylsulfonic acid and CBZ-DNPS-TRP-aminopropylsulfonic acid were carried out according to the basic procedure of Example 1, except that aminomethylsulfonic acid, or 3-amino,1-propane sulfonic acid were used, respectively, instead of taurine.

Synthesis of tBoc-DNPS-TRP-aminomethylsulfonic acid, tBoc-DNPS-TRP-aminoethylsulfonic acid, and tBoc-DNPS-TRP-aminopropylsulfonic acid were performed by the same basic procedure but starting from tBoc-TRP-OSU, and coupling it to either aminomethyl-, aminoethyl- or aminopropylsulfonic acid.

EXAMPLE 3

Figure 1:
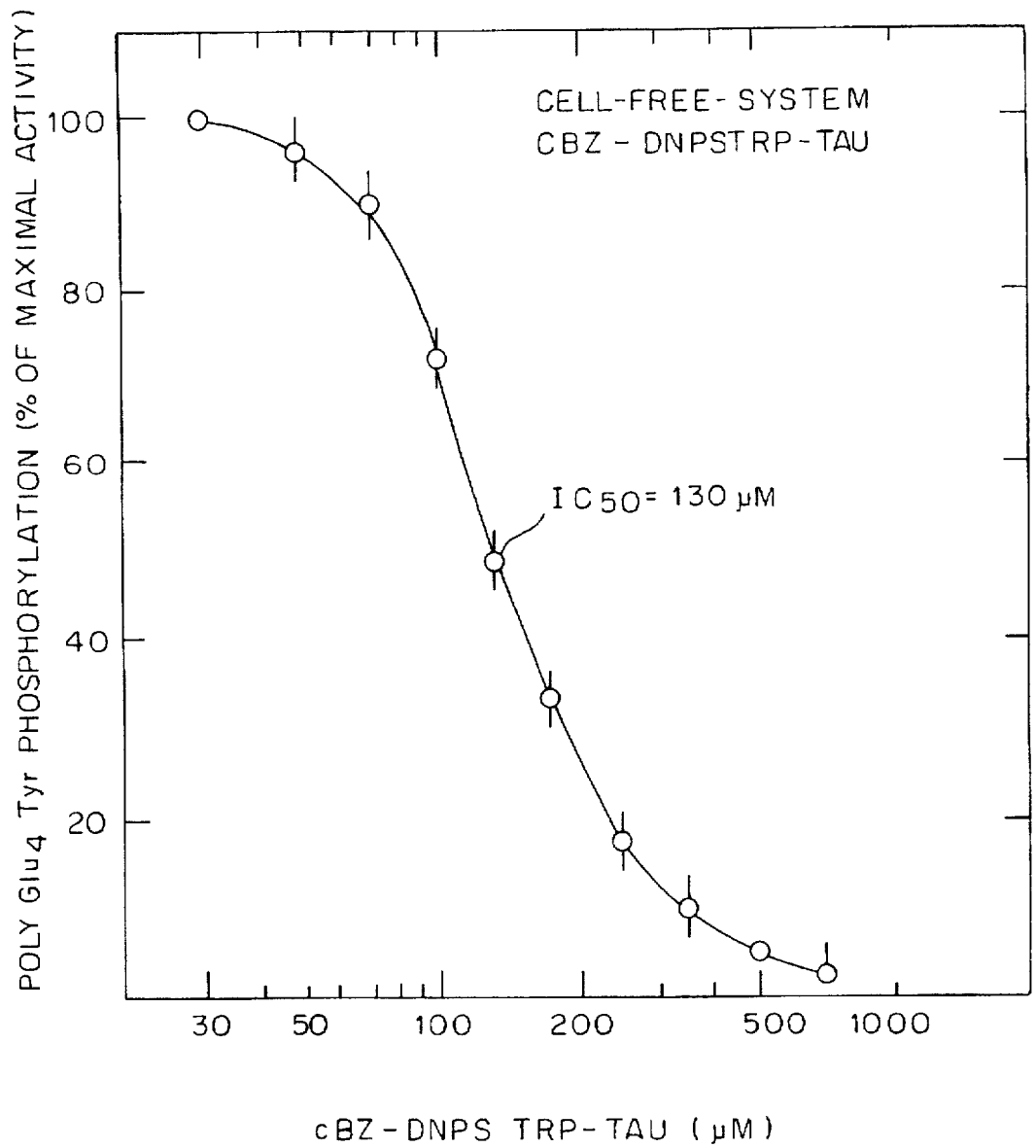
FIG. 1 shows dose-dependent inhibition of insulin receptor tyrosine kinase (InSRTK)-mediated PolyGlu$_4$Tyr phosphorylation by the compound herein designated CBZ-DNPS-TRP-TAU.

Dose-dependent inhibition of insulin receptor tyrosine kinase (InsRTK)-mediated PolyGlu$_4$Tyr phosphorylation by CBZ-DNPS-TRP-TAU An assay of PolyGlu$_4$Tyr phosphorylation by partially purified insulin receptor was run for 30 min at 22° C. in 60 μl of 50 mM Hepes (pH 7.4)–0.1% Triton X-100 containing wheat-germ-agglutinin purified rat liver insulin receptor (1 μg protein), MgCl$_2$ 25 mM; MnCl$_2$, 1 mM, ATP 17 μM, insulin 0.1 μM, PolyGlu$_4$Tyr, 0.17 mg/ml and the indicated concentrations in FIG. 1 of CBZ-DNPS-TRP-TAU. Phosphotyrosine content in PolyGlu$_4$Tyr was determined by a radioimmunoassay procedure (Shisheva et al., 1991). As shown in FIG. 1, CBZ-DNPS-TRP-TAU blocks InsRTK-dependent substrate phosphorylation in cell-free experiments (IC$_{50}$ value=130 μM). The inhibitory potency of other derivatives of formula I on InsRTK-catalyzed PolyGlu$_4$Tyr phosphorylation in cell-free experiments was determined. CBZ-NPS-TRP-TAU: IC$_{50}$ value=0.55 mM; CBZ-TRP-TAU: IC$_{50}$ value=2.7 mM; CBZ-TRP-β-TAU: IC$_{50}$ value=3.5 mM. For comparison, the IC$_{50}$ values for AC-TRP-TAU and L-tryptophan are 5 mM and >30 mM, respectively.

EXAMPLE 4

Dose-dependent inhibition of insulin- or vanadate-stimulated lipogenesis by CBZ-DNPS-TRP-TAU in rat adipocytes Rat adipocytes were prepared essentially by the method of Rodbell, 1964. The fat pads of three rats were cut into small pieces with scissors and digested in 3 ml of Krebs-Ringer-Bicarbonate (KRB)-buffer containing 0.7% bovine serum albumin (BSA) (pH 7.4) with collagenase (1 mg/ml). The digestion was performed in a 25 ml flexible plastic bottle under an atmosphere of carbogen (95% O$_2$, 5% CO$_2$) for 40 min at 37° C. with vigorous shaking. Five ml of buffer was then added, and the cells were squeezed through a mesh screen. The cells were then allowed to stand for several minutes (in a 15 ml plastic test tube at room temperature, floating) and the buffer underneath was removed. This procedure (suspension, floating and removal of buffer underneath) was repeated three times. For [$^{14}$C-U]glucose incorporation (lipogenesis), the fat cell suspensions (3×10$^5$ cells/ml) were divided into plastic vials (0.5 ml per vial) and incubated for 60 min at 37° C. under an atmosphere of 95%

Figure 2:
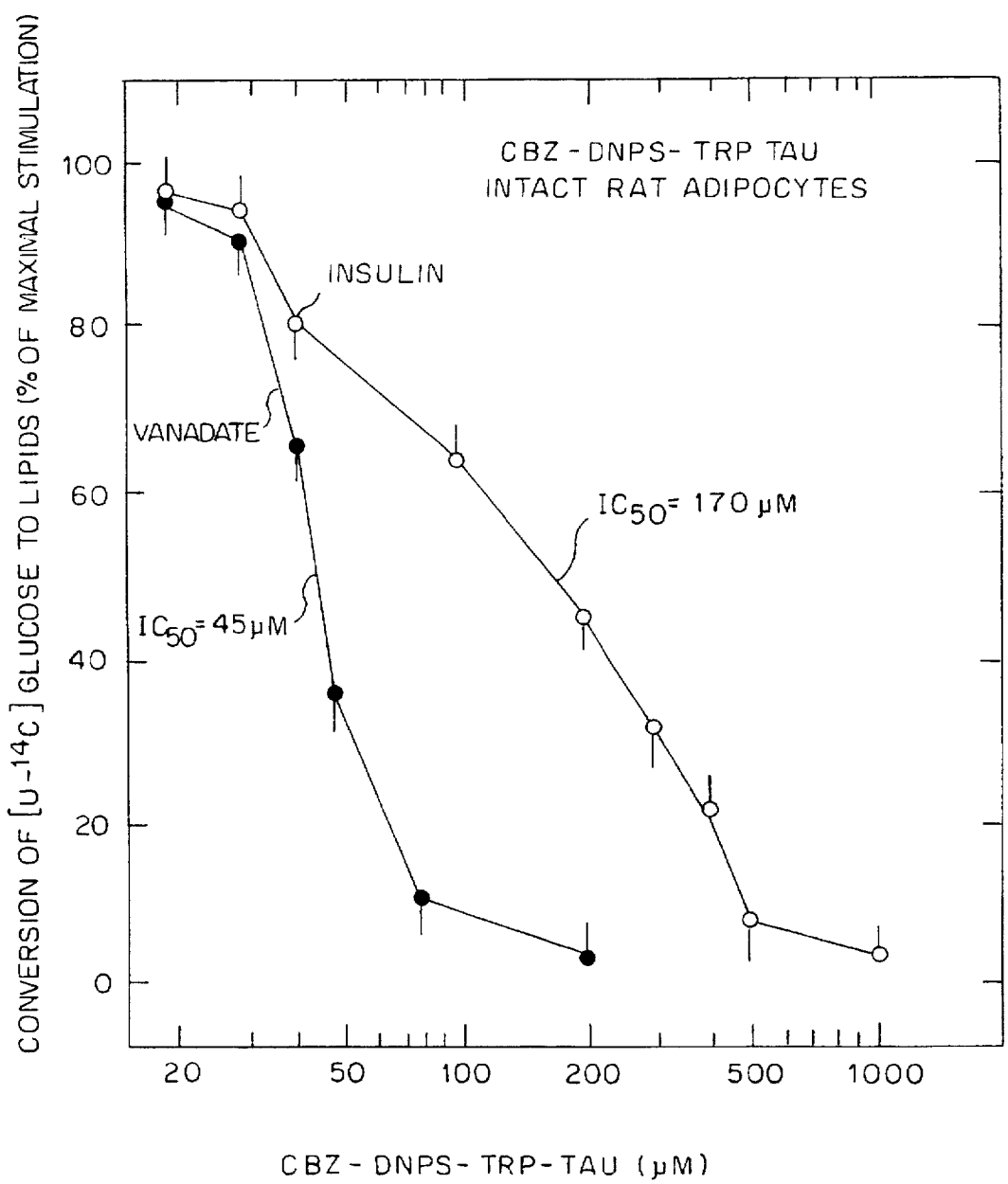
FIG. 2 shows dose-dependent inhibition of insulin- (empty circles) or vanadate- (filled circles) stimulated lipogenesis by CBZ-DNPS-TRP-TAU.

$O_2$, 5% $CO_2$, with 0.2 mM [U-$^{14}$C]glucose, in either the presence or absence of insulin (100 ng/ml) and the indicated concentrations in FIG. 2 of CBZ-DNPS-TRP-TAU. The reaction was terminated by adding toluene-based scintillation fluid (1.0 ml per vial) and the extracted lipids were counted (Shechter and Karlish, 1980). Fat cell suspensions were pre-incubated for 20 min at 37° C. with increasing concentrations of the inhibitors. Results are expressed in FIG. 2 as the percent of maximal stimulation at the indicated concentrations of inhibitors. In all experiments insulin-stimulated lipogenesis was 4- to 5-fold higher than basal; basal ~2000 cpm per $3\times10^5$ cells/h; $V_{insulin}$ 8000–10,000 cpm per $3\times10^5$ cells/h.

As shown in FIG. 2, CBZ-DNPS-TRP-TAU blocks insulin-dependent biological responses (such as lipogenesis) in intact rat adipocytes ($IC_{50}$=170 μM). Comparison of the dose-dependent inhibitions in cell-free system (FIG. 1) and in intact cellular system (FIG. 2) indicates that CBZ-DNPS-TRP-TAU exerts excellent permeability via the hydrophobic plasma membrane of mammalian cells into the cell interior. CBZ-DNPS-TRP-TAU also blocks the insulin-like effects of vanadate ions ($IC_{50}$=45 μM). The insulin-like effects of vanadium are mediated via another (non-insulin-receptor) cytosolic tyrosine kinase in rat adipocytes (Shisheva and Shechter, 1993).

EXAMPLE 5
Lack of inhibition of CBZ-DNPS-TRP-TAU on isoproterenol-mediated lipolysis In general there are two classes of protein kinases (PKs) in mammalian tissues: (a) PKs which phosphorylate tyrosine moieties in proteins (to phosphotyrosine), and (b) PKs which phosphorylate serine and threonine moieties (to phosphoserine and phosphothreonine). We wanted to confirm that CBZ-DNPS-TRP-TAU does not inhibit metabolic effects which are dependent on serine and threonine specific protein kinases. An example for such a metabolic effect is lipolysis which depends on protein kinase A. Rat adipocytes (prepared by the method of Rodbell, 1964) were incubated with isoproterenol alone (1 μM) or isoproterenol with CBZ-DNPS-TRP-TAU (200 μM) for one hour at 37° C. The amount of glycerol released from the cells was then determined by spectroscopic procedure (Shechter, 1982). As can be seen in Table I, CBZ-DNPS-TRP-TAU has negligible effect in inhibiting this metabolic effect.

TABLE I

Lack of inhibitory effect of CBZ-DNPS-TRP-TAU on isoproterenol-mediated lipolysis.

| Additions | Amount of glycerol released (nmol/3 × 10⁵ cells/3 h) | Percent lipolysis |
| --- | --- | --- |
| None | 10 | 0 |
| Isoproterenol, 1 μM | 165 | 100 |
| Isoproterenol, 1 μM plus CBZ-DNPS-TRP-TAU (200 μM) | 154 | 93 |

Figure 3:
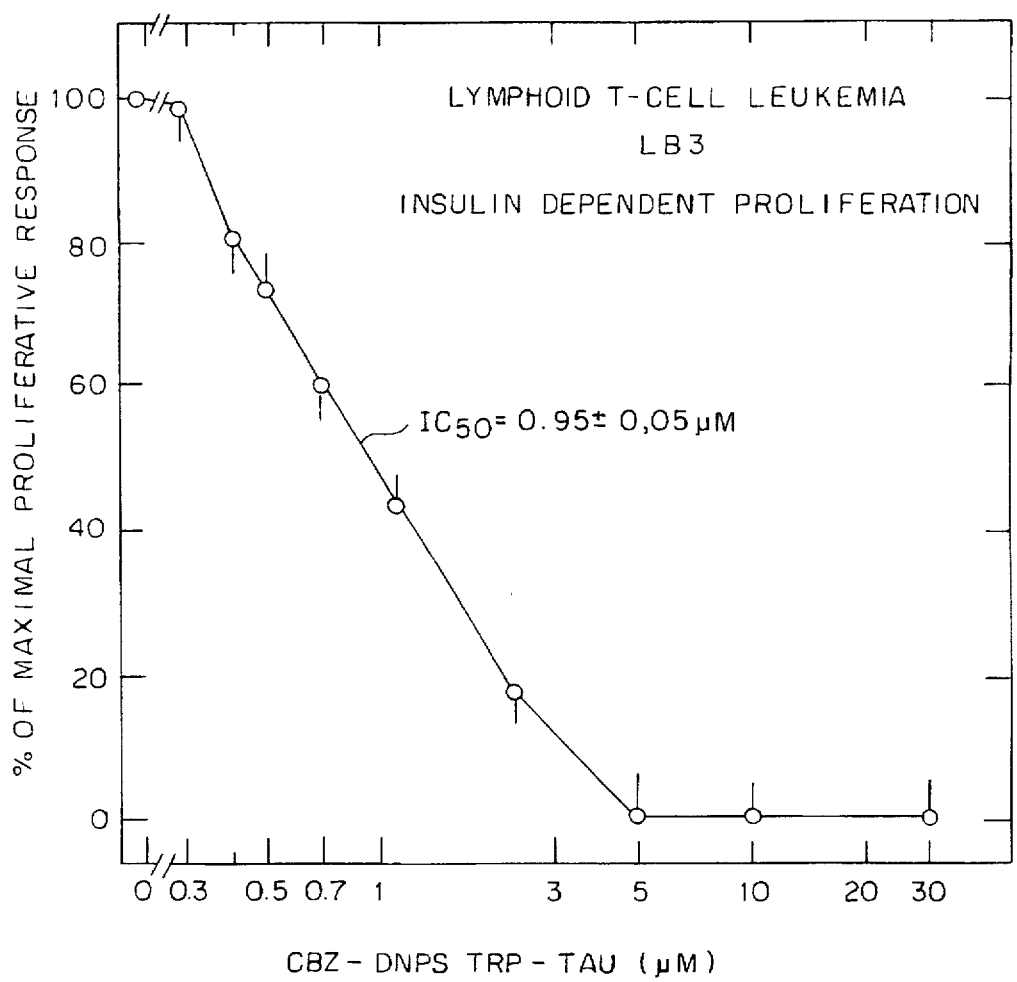
FIG. 3 shows inhibition of insulin-dependent proliferation of murine T-cell lymphoma (LB3) by CBZ-DNPS-TRP-TAU.

EXAMPLE 6
Inhibition of insulin-dependent proliferation of murine T-cell lymphoma (LB3) by CBZ-DNPS-TRP-TAU LB cells were removed from the peritoneal cavity of BALB/c mice, washed and resuspended in RPMI-1640. Then a continuous line designated LB3 was established in "LB medium" (50% RPMI-1640 plus 50% DCCM-1 in 10% fetal calf serum (FCS)). The LB3 cells were incubated (37° C., 5% $CO_2$) in microplate wells (Nunc, Roskilde, Denmark) with 0.2 ml RPMI-1640 alone and in the same medium containing insulin, fetal calf serum (FCS) or both, and different concentrations of the compound CBZ-DNPS-TRP-TAU as indicated in FIG. 3. Proliferation capacity was determined by thymidine incorporation ($^3$H-TdR, 1 μCi/well, specific activity 5 Ci/mM), added to the cells 24 hours later. In a typical experiment, cpm of $^3$H-thymidine incorporated into 30,000 cells was 12–14 fold higher in the presence of insulin or other mitogens than in their absence.

As shown in FIG. 3, CBZ-DNPS-TRP-TAU blocks insulin-dependent proliferation of murine T-cell lymphoma. Inhibition occurred with $IC_{50}$=0.95 μM, a concentration range nearly 200 times lower than that required to inhibit normal metabolic biological effects of insulin (see FIG. 2).

EXAMPLE 7
Inhibition of LB3 cell proliferation by CBZ-DNPS-TRP-TAU in response to various mitogens Experimental conditions were as described in Example 6 except that lower concentrations of mitogens were applied here (those triggering 50% of maximal proliferation): insulin, interleukin-2 (IL-2), growth hormone and PMA. PMA is an activator of protein kinase C. Protein kinase C in this cell type triggers proliferation by a pathway which is only partially dependent on endogenous tyrosine phosphorylation.

Figure 4:
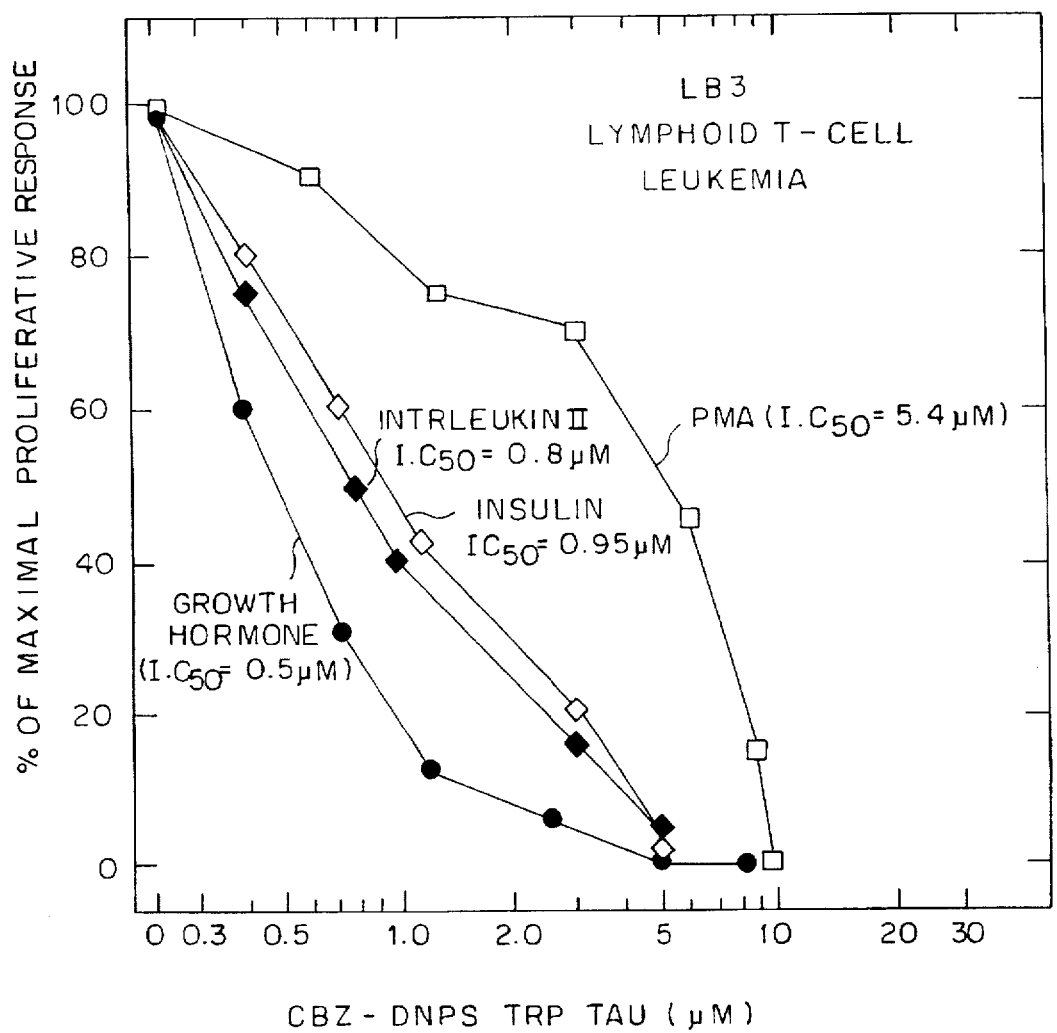
FIG. 4 shows inhibition of LB3 cell proliferation by CBZ-DNPS-TRP-TAU in response to various mitogens: empty squares—phorbol ester (PMA); empty losanges—insulin; filled losanges-interleukin-2 (IL-2); filled circles—growth hormone.

As shown in FIG. 4, CBZ-DNPS-TRP-TAU also blocks IL-2 and growth hormone-dependent proliferation of the T-cell lymphoma. Both agents utilize endogenous (cellular) tyrosine kinase activity to mediate their biological effects. In contrast, protein kinase C-dependent proliferation is inhibited by CBZ-DNPS-TRP-TAU at significantly higher concentrations.

In summary, the above examples show that CBZ-DNPS-TRP-TAU exhibits excellent permeability into cell interiors. Its inhibitory potency against malignant proliferation is ~200-fold greater as compared to its efficacy in arresting normal anabolic processes, both of which are dependent on endogenous tyrosine phosphorylation.

EXAMPLE 8
Relative potencies of various derivatives in cell-free and intact cell systems Various derivatives according to the invention in which $R^1$ is benzyloxycarbonyl (CBZ) or t-butoxycarbonyl (t-Boc), $R^2$ is —$SO_3H$ or —$PO_3H$, n is 1,2 or 3, and $R^3$ is H, 2-nitrophenylthio (NPS) or 2,4-dinitrophenylthio (DNPS) were prepared and examined in cell-free and intact cell systems. The cell-free assay is PolyGlu$_4$Tyr phosphorylation by partially purified insulin receptor as described in Example 3. The assay in intact cells (namely, lipogenesis) was carried out as described in Example 4.

The results in Table II demonstrate that sulfonates ($R^2$ is $SO_3H$) are at least 10 fold more effective than phosphonates ($R^2$ is —$PO_3H$) or carboxylates ($R^2$ is —COOH for example, CBZ-DNPS-TRP-Aspartic Acid). Also, both in vitro and in vivo, DNPS-TRP derivatives are more potent than NPS-TRP derivatives, which are more potent than non-substituted TRP derivatives ($R^3$ is H) and than leucine derivatives used for comparison.

The $R^1$ radical has to be a group conveying desirable hydrophobicity. Thus, although acetyl-DNPS-TRP-TAU inhibits InSRTK in cell-free experiments, it is not suitable because it exhibits low permeability into cell interiors.

TABLE II

Relative potencies of various derivatives in cell free and in intact cell systems.

| Derivative designation | Relative cell-free potency in inhibiting InsRTK % | Permeability into cell interiors |
|---|---|---|
| CBZ-DNPS-TRP-Taurine | 100 | excellent |
| CBZ-DNPS-TRP-aminomethyl-SO$_3$ | 90 | excellent |
| CBZ-DNPS-TRP-aminopropyl-SO$_3$ | 70 | excellent |
| CBZ-NPS-TRP-Taurine | 30 | good |
| tBoc-DNPS-TRP-Taurine | 95 | excellent |
| tBoc-DNPS-TRP-aminomethyl-SO$_3$ | 80 | excellent |
| tBoc-DNPS-TRP-aminopropyl-SO$_3$ | 90 | excellent |
| Acetyl-DNPS-TRP-Taurine | 80 | poor |
| CBZ-TRP-Taurine | 20 | poor |
| CBZ-TRP-aminomethyl-PO$_3$ | 5 | poor |
| CBZ-leucine-Taurine | 2 | poor |
| CBZ-DNPS-TRP-Aspartic Acid | 5 | good |

EXAMPLE 9

BALB/c mice were inoculated intraperitoneally (i.p.) each with 100 LB3 cells. Thirty minutes later the mice were injected i.p. with 50–200 μM of the compound of formula I (e.g. CBZ-DNPS-TRP-TAU), and the injections were repeated every other day for 3 weeks. Control mice were inoculated with LB3 cells only. At the end of the experiment, the survival time of the treated mice is determined.

REFERENCES

Bishop, J. M. (1987) The molecular genetics of cancer. Science 335, 305–311.
Elder et al. (1989) Science 243, 811–814.
Graziani, Y. Chayoth, R., Karny, N., Feldman, B. and Levy, J. (1981) Biochim. Biophys. Acta 714, 415–421.
Graziani, Y., Erikson, E. and Erikson, R. L. (1983) Eur. J. Biochem. 135, 583–589.
Levitzki, A. (1992) FASEB J. 6, 3275–3282.
Rodbell, M. (1964) J. Biol. Chem. 239, 375–380.
Ross, T. (1989) Platelet derived growth factor. Lancet 1, 1179–1182.
Shechter, Y. (1982) Endocrinology 110, 1579–1583.
Shisheva, A. and Shechter, Y. (1993) J. Biol. Chem. 268, 6463.
Shisheva, L. A., Leithner, O. and Shechter, Y. (1991) J. Biol. Chem. Methods 23, 307–314.

We claim:

1. A compound of the formula I:

$$R^1-NH-CH-CONH(CH_2)_n-R^2 \quad (I)$$

[indole structure with CH$_2$ linker and R$_3$ substituent]

wherein
R$^1$ is a hydrophobic group which is a radical selected from the group consisting of C$_5$–C$_{20}$ alkyl, C$_5$–C$_{20}$ alkenyl, C$_5$–C$_{20}$ carboxylic acyl, C$_3$–C$_8$ alkoxycarbonyl, C$_5$–C$_8$ cycloalkoxycarbonyl, and unsubstituted or chloro-substituted benzyloxycarbonyl;

R$^2$ is a radical selected from —COOH, —SO$_3$H and —PO$_3$H;

R$^3$ is H, or a radical selected from phenylthio and pyridythio substituted by one or two nitro groups;

n is 1 to 3, and pharmaceutically acceptable salts thereof.

2. A compound according to claim 1 wherein R$^1$ is t-butoxycarbonyl.

3. A compound according to claim 1 wherein R$^1$ is unsubstituted benzyloxycarbonyl.

4. A compound according to claim 1 wherein R$^2$ is —SO$_3$H.

5. A compound of the formula

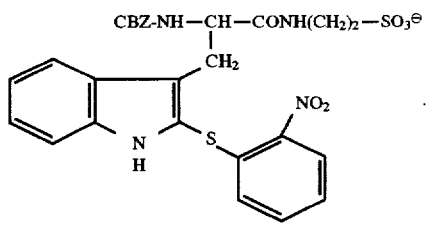

6. A compound herein of the formula:

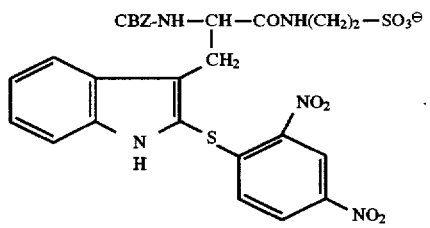

7. A pharmaceutical composition comprising a pharmaceutically acceptable carrier and an effective amount of a compound in accordance with claim 1.

8. A pharmaceutical composition according to claim 8 wherein said compound is of the formula:

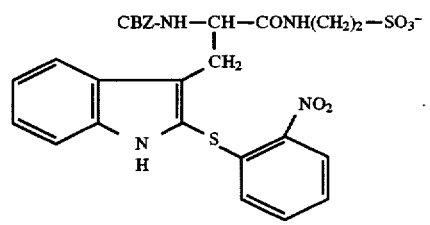

* * * * *